US00PP33274P2

(12) United States Plant Patent
Van Swieten

(10) Patent No.: US PP33,274 P2
(45) Date of Patent: Jul. 20, 2021

(54) ***PHALAENOPSIS* ORCHID PLANT NAMED 'PHALGITZE'**

(50) Latin Name: ***Phalaenopsis* hybrid**
Varietal Denomination: PHALGITZE

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/974,421

(22) Filed: Jan. 27, 2021

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALGITZE', particularly characterized by small, greenish-yellow, striped flowers with dark reddish-orange and purplish-pink lips, slightly raised calluses, oblong lateral lobes of the lip, a short and compact plant, and is propagated by meristem tissue culture, is disclosed.

3 Drawing Sheets

Genus and species: *Phalaenopsis* hybrid.
Variety denomination: 'PHALGITZE'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGITZE'.

The new *Phalaenopsis* plant is a product of a planned breeding program conducted by the inventor in Bleiswijk, the Netherlands. The objective of this breeding program was to create a new, short *Phalaenopsis* plant with numerous attractive and unique, small, greenish-yellow, striped flowers with dark reddish-orange and purplish-pink lips, suitable for potted plant production.

The new *Phalaenopsis* plant 'PHALGITZE' is a result of cross-pollination made by the inventor in May 2010 in Bleiswijk, the Netherlands, of the proprietary female, or seed parent, *Phalaenopsis* hybrid '21864-012' (unpatented) with the proprietary male, or pollen parent, *Phalaenopsis* hybrid '17414-03' (unpatented).

The new *Phalaenopsis* was selected by the inventor as a single plant within the progeny of the stated cross-pollination in a controlled greenhouse in Bleiswijk, the Netherlands, in May 2013. Asexual reproduction of the new *Phalaenopsis* plant by meristem tissue culture since 2014 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Aug. 30, 2019 (Application no. 2019/2060), by Applicant who obtained the subject matter disclosed directly from the inventor. 'PHALGITZE' has not been made publicly available or sold anywhere in the world prior to the effective filing date of this application with the exception of sales or disclosures made one year or less before the effective filing date of this claimed invention by Applicant who obtained 'PHALGITZE' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGITZE' as a new and distinct variety of *Phalaenopsis* plant:

1) Small, greenish-yellow, striped flowers with dark reddish-orange and purplish-pink lips;
2) Callus is slightly raised;
3) Lateral lobe of the lip is oblong; and
4) Plant is short and compact.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in December 2020. Colors in the photographs may differ from the color values cited in the detailed botanical description, which accurately describe the actual colors of the new variety.

DESCRIPTION OF THE NEW VARIETY

Figure 1:
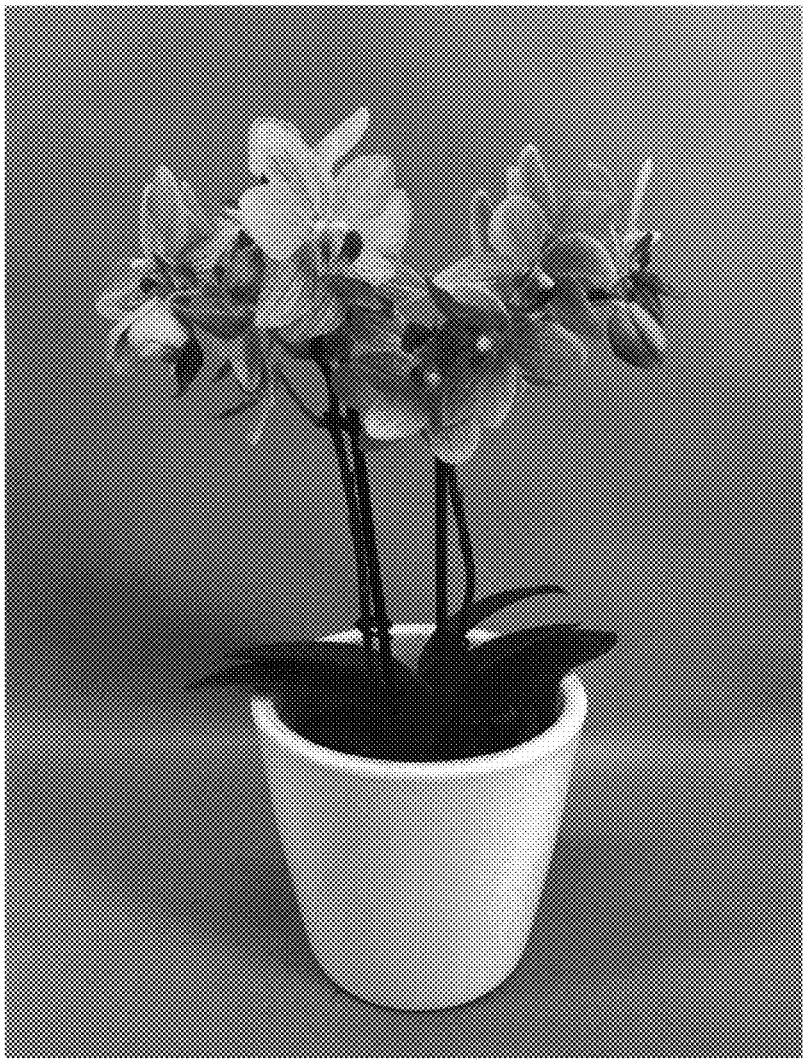
FIG. 1 shows the overall plant habit, including blooms, buds, and foliage of 'PHALGITZE'.
Figure 2:
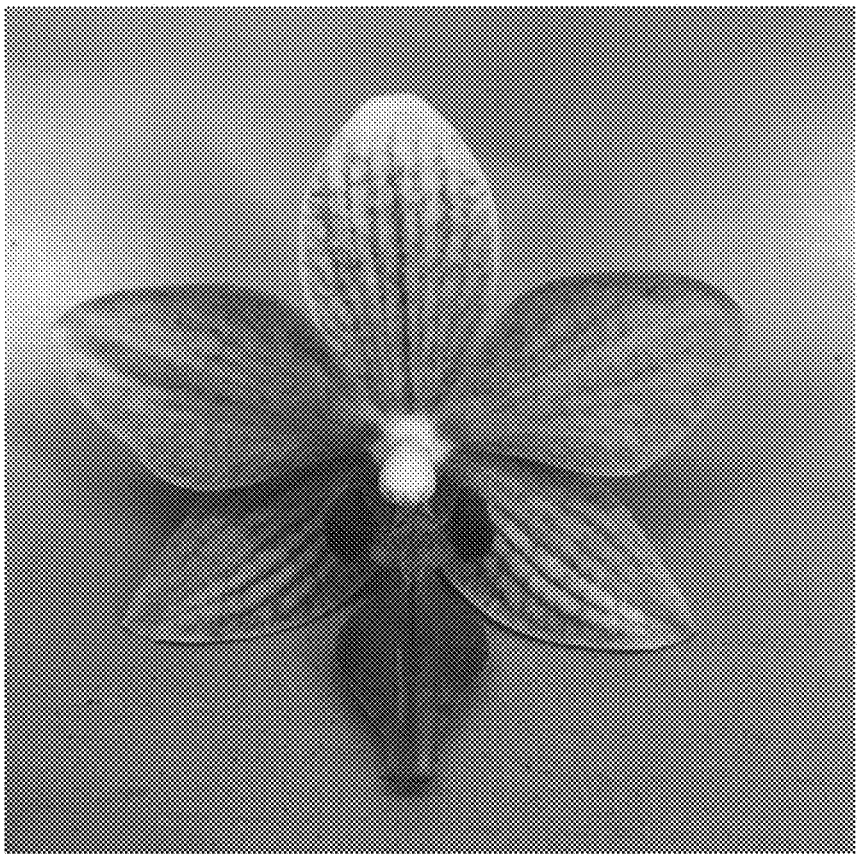
FIG. 2 shows a close-up of a flower of 'PHALGITZE'.
Figure 3:
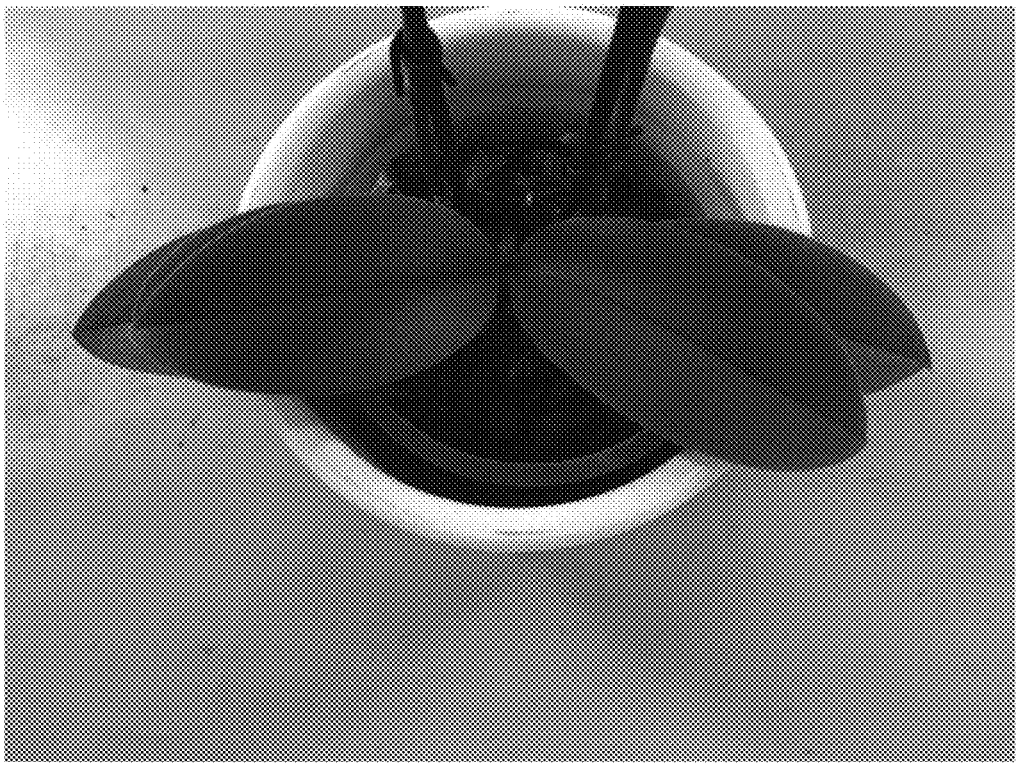
FIG. 3 shows an overhead view of the leaves of 'PHALGITZE'.

The following detailed description sets forth the distinctive characteristics of 'PHALGITZE'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in December 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGITZE'.

Parentage:

*Female parent*.—*Phalaenopsis* cultivar '21864-012' (unpatented).

*Male parent*.—*Phalaenopsis* cultivar '17414-03' (unpatented).

Propagation:

*Type*.—Meristem tissue culture.

Roots:

*Root description*.—Greyed-green (a color in between RHS 190B and 190C) colored roots with branching lateral roots having yellow-green (a color in between RHS N144C and N144D) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme and panicle inflorescence.

*Height* (*from soil level to top of inflorescence*).—Approximately 22.0 cm to 27.0 cm.

*Width* (*measured from leaf tips*).—About 21.0 cm to 23.0 cm.

*Vigor*.—Strong.

Leaves:

*Mature leaves*.—Quantity per plant: 6 to 8 leaves are produced before flowering. Length (fully expanded): 9.0 cm to 12.0 cm. Width: 4.0 cm to 5.0 cm. Position of the broadest part of the leaf: At the middle. Shape: Narrow oblong. Base shape: Moderately to slightly elongated. Apex: Obtuse asymmetric. Leaf blade angle with the petiole (measured from the horizontal position): Between 15 degrees and 30 degrees. Leaf margin: Entire. Color: Upper surface: RHS 146A. Lower surface: RHS 146B. Texture (both upper and lower surfaces): Smooth. Thickness: 1.9 mm to 2.2 mm. Variegation: Absent. Venation: Pattern: Parallel. Color of the midvein: Upper surface: A color in between RHS 187B and 200B. Lower surface: RHS 187B.

Peduncle:

*Quantity per plant*.—1 to 2.

*Number of flowers per peduncle*.—10 to 13.

*Length*.—22.0 cm to 27.0 cm.

*Diameter*.—3.0 mm to 4.0 mm.

*Strength*.—Strong.

*Aspect*.—Upright to slightly pendent.

*Texture*.—Smooth.

*Color*.—Yellow-green (RHS 146C) with a touch of brown (RHS 200B).

*Internode length*.—2.0 cm to 3.0 cm.

Inflorescence description:

*Appearance*.—Upright to slightly pendent, raceme and panicle inflorescence with bilaterally symmetrical flowers that open in succession beginning with the lowermost flower.

*Number of inflorescences*.—1 to 2.

*Inflorescence size*.—Height (from base to tip): 110.0 mm to 130.0 mm.

*Flowering time*.—First flowers can be expected 10 to 11 months after planting in a 12-cm pot.

*Flower*.—Height: 50.0 mm to 55.0 mm. Diameter: 50.0 mm to 55.0 mm. Depth of lip: About 26.0 mm to 28.0 mm.

*Flower longevity*.—On the plant: 8 to 10 weeks.

*Flower shape*.—Flat.

*Fragrance*.—Absent.

*Flower bud*.—Average size: Medium to large. Length: 21.0 mm to 23.0 mm. Width: 14.0 mm to 16.0 mm. Shape: Egg shaped. Color: Yellowish-green (a color in between RHS N144A and N144D) with diluting reddish stripes (RHS 182B).

*Petals*.—Arrangement: Open. Shape: Semi-circular. Apex: Obtuse asymmetric. Margin: Entire. Length (from base to tip): 27.0 mm to 29.0 mm. Width: 19.0 mm to 21.0 mm. Position of the broadest part of the petal: At the middle. Color (when fully opened): Upper surface: Basic color: Greenish-yellow (RHS 6B) toward margin. Over color: Reddish-brown stripes (RHS 176B). Lower surface: Basic color: Greenish-yellow (a color in between RHS 1B and 151B). Over color: Diluting light reddish-brown stripes (RHS 177B) toward margin. Number of spots and stripes on the petals (upper surface): Medium stripes. Color of spots and stripes on the petals (upper surface): RHS 176B. Density of netting of the petals (upper surface): None. Color of the netting (upper surface): None.

*Dorsal sepal*.—Shape: Elliptic. Apex: Flat symmetric. Margin: Entire. Length (from base to tip): 31.0 mm to 33.0 mm. Width: 16.0 mm to 18.0 mm. Position of the broadest part of the dorsal sepals: At the middle. Color (when fully opened): Upper surface: Basic color: Greenish-yellow (RHS 1A). Over color: Red stripes (RHS 176A). Lower surface: Basic color: Greenish-yellow (a color in between RHS 1B and 151B). Over color: Diluting reddish-orange stripes (RHS 177C). Number of spots and stripes on the dorsal sepals (upper surface): Medium to many stripes. Color of spots and stripes on the dorsal sepals (upper surface): RHS 176A. Density of netting of the dorsal sepals (upper surface): None. Color of the netting: None.

*Lateral sepals*.—Shape: Ovate. Apex: Obtuse asymmetric. Margin: Entire. Length (from base to tip): 29.0 mm to 31.0 mm. Width: 16.0 mm to 18.0 mm. Position of the broadest part of the lateral sepals: Toward the base. Color (when fully opened): Upper surface: Basic color: Greenish-yellow (RHS 151B). Over color: Light greenish-yellow (RHS 4B) on side; striped (a color in between RHS 176A and 176B) and very small dots (RHS 176A) at the base. Lower surface: Basic color: Greenish-yellow (RHS 151B). Over color: Diluting reddish-orange stripes (RHS 177C). Number of spots, dots, and stripes on the lateral sepals (upper surface): Medium stripes and medium of very small dots at the base. Color of spots, dots, and stripes on the lateral sepals (upper surface): Stripes are a color in between RHS 176A and 176B and dots are RHS 176A. Density of netting of the lateral sepals (upper surface): None. Color of the netting (upper surface): None.

*Labellum* (*lip*).—Whiskers: Present, but very short. Length of whiskers: 1.0 mm to 2.0 mm. Color of whiskers: Purplish-red (RHS 186A) with white tips (RHS NN155C). Pubescence on the lip: Absent.

*Lateral lobe*.—Shape: Type III (as described in the International Union for the Protection of New Varieties of Plants (UPOV) Test Guidelines for *Phalaenopsis*); oblong. Margin: Slightly undulated. Length: 11.0 mm to 13.0 mm. Width: 4.0 mm to 6.0 mm. Color: Upper surface: Greenish (RHS 6B); dotted (RHS 181A) at the base; red (RHS 184B) and purplish-red (RHS 185C) toward the tip. Lower surface: Greenish-yellow (RHS 6C) at the base; light greenish-yellow (RHS 160C) at the middle toward the tip and red (RHS 181A) toward the margin. Number of spots and stripes on the lateral lobe: Few very small spots at the base. Color of spots and stripes on the lateral lobe: RHS 181A. Density of netting of the lateral lobe: None. Color of the netting: None.

*Apical lobe*.—Shape: Ovate to elliptic. Margin: Entire. Length: 18.0 mm to 20.0 mm. Width: 17.0 mm to 19.0 mm. Color: Upper surface: Hint of yellow (RHS 13A) and dark reddish-orange (RHS 178A) at the base; purplish-red (RHS 186B) and dark purplish-pink (RHS 186C) toward whiskers. Lower surface: Touch of light yellow (a color in between RHS 163C and 163D) at the base; white (RHS 155C) at the middle toward whiskers and touch of purplish-pink (RHS N78C) toward margin. Number of spots and stripes on the apical lobe: None. Color of spots and stripes on the apical lobe: None. Density of netting of the apical lobe: None. Color of the netting: None. Bump and ridge: Medium.

*Callus*.—Average size: Very small to small. Height: 3.0 mm to 4.0 mm. Length: 2.0 mm to 3.0 mm. Width: 3.0 mm to 4.0 mm. Color: Yellow tips (RHS 12A); light greenish-yellow (RHS 8B) on sides; dotted (RHS 176A).

Reproductive organs:

*Column*.—Length: 8.0 mm to 10.0 mm. Diameter: 3.9 mm to 4.3 mm. Color: Very light purple (RHS 76B) at the base with white tip (RHS NN155C).

*Pollinia*.—Quantity: 2. Diameter: 0.4 mm to 0.6 mm. Color: Orange (RHS 24A).

*Ovary*.—Length: 9.0 mm to 11.0 mm. Diameter: 1.3 mm to 1.6 mm.

*Pedicel*.—Length: 31.0 mm to 33.0 mm. Diameter: 1.7 mm to 2.0 mm. Texture: Smooth. Color: Yellow-green (RHS 144C) at the base and light yellow-green (RHS 145C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGITZE' differs from the female parent plant '21864-012' (unpatented) in that 'PHALGITZE' has flowers with a striped pattern and very short whiskers, whereas '21864-012' has flowers with a spotted pattern at the base and no whiskers. Additionally, 'PHALGITZE' has smaller flowers than '21864-012'.

'PHALGITZE' differs from the male parent plant '17414-03' (unpatented) in that 'PHALGITZE' has flowers with a main color of greenish-yellow and very short whiskers, whereas '17414-03' has flowers with a main color of purple and no whiskers. Additionally, 'PHALGITZE' has larger flowers than '17414-03'.

'PHALGITZE' is most similar to the commercial *Phalaenopsis* plants named 'PHALYPBE' (U.S. Plant patent application Ser. No. 16/923,579) and 'PHALGALYI' (U.S. Plant Pat. No. 31,051). 'PHALGITZE' differs from the commercial variety 'PHALYPBE' in that 'PHALGITZE' has ovate to elliptic apical lobes, whereas 'PHALYPBE' has rhombic apical lobes. Additionally, 'PHALGITZE' has narrower petals than 'PHALYPBE'.

'PHALGITZE' differs from the commercial variety 'PHALGALYI' in that 'PHALGITZE' has purplish-red whiskers with white tips and oblong lateral lobes, whereas 'PHALGALYI' has greenish-yellow whiskers and weakly spatulate lateral lobes. Additionally, 'PHALGITZE' has narrower petals than 'PHALGALYI'.

I claim:

1. A new and distinct variety of *Phalaenopsis* plant named 'PHALGITZE', substantially as described and illustrated herein.

* * * * *